(12) United States Patent
Moss

(10) Patent No.: US 6,949,092 B1
(45) Date of Patent: Sep. 27, 2005

(54) CONTINUOUS FEEDING AND DECOMPRESSING DEVICE, TUBE ASSEMBLY, AND METHODS

(76) Inventor: Gerald Moss, 1 Reynal Rd., White Plains, NY (US) 10605

( * ) Notice: Subject to any disclaimer, the term of this patent is extended or adjusted under 35 U.S.C. 154(b) by 21 days.

(21) Appl. No.: 10/655,891

(22) Filed: Sep. 5, 2003

Related U.S. Application Data

(63) Continuation-in-part of application No. 10/419,036, filed on Apr. 18, 2003.

(51) Int. Cl.[7] ............................................. A61M 31/00
(52) U.S. Cl. ....................................................... 604/508
(58) Field of Search ................................ 604/523, 534, 604/535, 538, 158, 159, 171, 173, 176, 264, 604/276, 246

(56) References Cited

U.S. PATENT DOCUMENTS

| | | |
|---|---|---|
| 3,054,401 A | 9/1962 | Geweche |
| 4,270,533 A | 6/1981 | Andreas |
| 4,396,382 A | 8/1983 | Goldhaber |
| 4,543,089 A | 9/1985 | Moss |
| 4,576,603 A | 3/1986 | Moss |
| 4,642,092 A | 2/1987 | Moss |
| 4,685,901 A * | 8/1987 | Parks ..................... 604/103.03 |
| 5,318,556 A | 6/1994 | Avallone et al. |
| 5,520,662 A | 5/1996 | Moss |
| 6,364,864 B1 | 4/2002 | Mohiuddin et al. |
| 6,447,472 B1 | 9/2002 | Moss |
| 6,468,259 B1 | 10/2002 | Loretti et al. |

* cited by examiner

Primary Examiner—Kevin C. Simmons
(74) Attorney, Agent, or Firm—Schmeiser, Olsen & Watts LLP

(57) ABSTRACT

A decompressing and feeding device for safely feeding in the gastrointestinal tract of a recovering patient continuously aspirates and feeds at a rate commensurate with the ability of the intestines to absorb fluids including nutrient. Air is also aspirated in the process so that neither air nor excess fluids cause distension in the gastrointestinal tract. Digestive juices and nutrients that are aspirated are continuously refed together with unused feeding material into the gastrointestinal tract at a location that more efficiently moves and digests the food. The device may include two aspirate reservoirs to and from which aspirate is alternatingly transferred. To provide the continuous and alternating flow, a solenoid valve and timer switch device is provided. Alternatively, a device with a single aspirate reservoir to which and from which aspirate is transferred can be used. A feeding and aspirating tube assembly having a plurality of separable lumens can be incorporated.

3 Claims, 5 Drawing Sheets

CONTINUOUS FEEDING AND DECOMPRESSING DEVICE, TUBE ASSEMBLY, AND METHODS

This application is a continuation-in-part of patent application Ser. No. 10/419,036, filed Apr. 18, 2003, and entitled "CONTINUOUS FEEDING AND DECOMPRESSING DEVICE AND METHOD", the disclosure of which is incorporated herein by reference.

BACKGROUND OF THE INVENTION

1. Technical Field

This invention generally relates to a device used to aspirate a gastro-intestinal tract and/or to deliver nutrients, fluids, medication, and/or aspirate into the gastro-intestinal tract. The invention specifically relates to devices including feeding tubes, and methods for safely, efficiently, and/or continuously aspirating from and feeding into the gastro-intestinal tract.

2. Background Art

Frequently, hospital patients are unable to consume food normally. In these situations, it is often necessary to use a feeding tube to provide nutrition, fluids, and/or medicine. Such a tube is inserted into a patient's gastro-intestinal tract through the nose (nasogastric or nasoenteric tubes) or surgically by means of a gastrostomy or jejunostomy. Because adequate nutritional intake facilitates recovery, the proper use of a feeding tube and an associated device for feeding through the feeding tube can greatly benefit a patient.

However, the feeding tubes and the associated devices and methods also pose some discomfort, and even some potential risks, to patients. A number of commercially available feeding tubes exist. Unfortunately, all presently available feeding tube devices and methods for feeding through the tubes suffer from a variety of deficiencies. One common problem is that a feeding tube may deliver the fluids (which include liquid nutrition, hydrating fluids, and medicine to the patient) at a rate exceeding the ability of the gastro-intestinal tract to absorb such fluids. This results in an accumulation of fluid within the intestine. In particularly bad cases, accumulation of fluid causes distension of the intestine that leads to the temporary loss of all residual intestinal function. In rare cases, this intestinal distention may induce fatal vagal reflex circulatory changes. Approximately 1 in 1000 patients that are fed through a jejunal tube die of bowel necrosis, a complication that may be related to the lack of safety of the devices and methods of feeding directly into the gastro-intestinal tract. Severely ill, malnourished patients are most at risk for developing complications associated with over-feeding. Aside from being at high risk, these patients are also most in need of the earliest optimum nutrition. In any case, when a patient's intestine is not operating fully, then the amount of nutrition the patient can receive is limited. However, adequate nutrition is obviously a critical part of anyone's health and is necessary in order to provide optimum recovery for a patient. It is thus desirable to deliver as much nutrition to a patient as can be absorbed safely by the patient's impaired gastro-intestinal tract. Devices and methods of the past are deficient in providing this maximum feeding in a safe, prompt, and effective way to patients in need.

It is not desirable to simply deliver a maximum amount of nutrition into a patient's intestine. The reason for this is that overfeeding, which is delivering feedings at a rate exceeding the ability of the patient's gastro-intestinal tract to absorb its own secretions plus the added nutrition, itself presents serious hazards to a patient. Overfeeding a patient leads to an accumulation of fluid, which distends the intestine. This intestinal distension can lead to fatal circulatory changes, as set forth above. More commonly, complications from overfeeding include the temporary further impairment of intestinal function, with nausea and vomiting, which at a minimum causes discomfort and delays recovery. A common and more severe related complication is impaired ability to breathe deeply and cough because of abdominal distention, resulting in atelectasis and pneumonia.

A patient's impaired digestive system may also produce too many digestive secretions for the patient to reabsorb immediately. A typical person secretes seven to eight liters of fluid per day, starting with saliva. All secretions normally are reabsorbed by the intestine, without net loss or gain of fluid for the body. Unfortunately, during recovery from surgery the level of secretions remains relatively constant or decreases, while the intestine's ability to absorb secretions is typically impaired, sometimes severely. The result can be a build up of fluid in the intestine, with the same detrimental side effects as found with over-feeding. The problem of digestive secretions can be exacerbated by feeding.

When concentrated nutrition is delivered to a patient's gastro-intestinal tract, the body's natural response is to produce digestive secretions to dilute the feedings and break down the complex nutrients for absorption by the intestine. However, if a patient's gastro-intestinal function is severely impaired only a portion of the total fluid may be absorbed. By way of example, for 2 ml of nutrition delivered to the gastro-intestinal tract, 10 ml of digestive secretions may be provided in response. The intestine may temporarily be capable of absorbing only 2 ml of fluid, resulting in a net increase of 10 ml to the volume of fluid in the gastro-intestinal tract. Thus, nutrition delivered to the intestine may be competing with digestive secretions for absorption by the intestine. This problem may worsen as feedings continue, causing progressive intestinal distension which, in turn, further impairs intestinal function and reduces the amount of nutrient actually being absorbed. To avoid problems of overfeeding or excessive secretion build up during recovery, a patient's gastrointestinal tract may be aspirated to remove excessive fluid. However, any secretions removed in this way will cause a net loss of fluids and dehydration of the patient. Past solutions to this problem include providing replacement fluids in the form of an intravenous saline solution. However, this method of fluid replacement does not conserve nutrients and digestive juices that may have otherwise been used.

Another problem that has not adequately been solved is that the very presence of a nasal feeding tube stimulates swallowing by the patient, introducing additional air into the intestine. The presence of air within the gastro-intestinal tract interferes with the propulsion and absorption of nutrition and can be quite uncomfortable or painful to a patient. The use of an aspirating tube to remove air from the gastro-intestinal tract has been used to combat this problem. As set forth above, aspirating introduces additional problems of increased risks of dehydration and removal of potentially beneficial nutrients.

Unfortunately, the use of a second tube for aspiration presents new problems. The introduction of a second tube only adds to the pain and discomfort experienced by a patient. Furthermore, if a separate second tube is used, it may be difficult to effectively locate it proximate to the feeding tube, thereby preventing it from aspirating excessive food present in the gastro-intestinal tract.

In conjunction with systems of the past that have been used for feeding and aspirating, tubes with more than one lumen integrated in a single tube have been used. These tubes are typically manufactured with a plurality of lumens that are permanently formed as part of the tubes. Thus, the feeding tubes of the past are deficient enabling assembly and disassembly after the time of manufacture. Furthermore, the manufacturing process required in order to make feeding and aspirating tubes having a plurality of permanent lumens is relatively expensive and intricate.

DISCLOSURE OF THE INVENTION

The present invention overcomes the many deficiencies of the past and has many advantages as will become apparent in the following disclosure and description. Accordingly, the invention relates to a device for providing as much nutrient to the gastro-intestinal tract as possible without overfeeding, for example, in a patient recovering from surgery. The invention also includes a device and a method that improves the efficiency of absorption in the gastro-intestinal tract by removing gas and by stepping a feeding material forward to a location in which greater peristaltic activity promotes greater absorption and flow. The device and method further reduce the tendency to dehydration of past devices and methods. The present invention incorporates the principles of the Applicant's prior inventions disclosed in U.S. Pat. No. 6,447,472, filed Oct. 19, 2000, and issued Sep. 10, 2002, the disclosure of which is incorporated herein by reference. The present invention has many added features, structural differences, and utilizes distinct methods. The new aspects safely provide continuous aspiration and continuous feeding and other advantages that have not been adequately addressed by devices and methods of the past.

It is to be explicitly understood that the devices and methods of the present invention are not limited to use in human patients, but may be used in veterinarian applications or even in other non-medical applications. Furthermore, it is to be understood that while the devices are specifically applicable in the gastro-intestinal tract of a body, the devices may also be useful in other organs or systems of the human. Therefore, the disclosure directed specifically to the application of the devices and methods for feeding and decompressing in the gastro-intestinal tract is to be considered exemplary and not restrictive. The limitations of the devices and methods are to be interpreted in accordance with the appended claims.

In one aspect, the invention comprises a feeding and decompression device for feeding into and aspirating from an intestinal tract. In this aspect, the device includes a first aspirate reservoir and a second aspirate reservoir each connected to an aspiration channel. A vacuum source is alternatingly fluidly connected to the first and the second aspirate reservoirs and induces a flow of an aspirate from the aspiration channel to at least one of the reservoirs at a time.

To facilitate the switching between the reservoirs, the device includes a solenoid valve connected to the first and second aspirate reservoirs and to the vacuum source. A timer switch connects a power source to the solenoid valve so that the timer switch and solenoid valve alternatingly fluidly connect the first and second aspirate reservoirs with the vacuum source. Furthermore, the timer switch and the solenoid valve connect the reservoir that is not connected to the vacuum source to a vent. Specifically, the first and second reservoirs can be continuously switched back and forth between being connected to the vacuum source and the vent so that one reservoir is always connected to the vacuum source and one is always connected to the vent.

In another aspect of the invention, the device simply comprises a solenoid valve and timer device for alternating valves of the device between positions. In this aspect, the device includes a solenoid and a valve housing having at least four connection points for connecting a plurality of fluid lines. The valve housing is connected to the solenoid such that the solenoid operatively controls at least two valves within the housing. The solenoid and timer device has an adjustable timer that meters time for a cycle of a predetermined period of the time. The adjustable timer is connected to the solenoid and to a switch so that the switch alternates between an open and a closed state for predetermined portions of the cycle. This cycle can be repeated indefinitely. A source of power is connected to the solenoid by a circuit that includes the switch. Thus, the switch is alternatingly closed and opened by the timer, whereby power from the power source is correspondingly applied to and removed from the solenoid. The power being repeatedly turned on and off causes the solenoid to simultaneously move the at least two valves between a first position and a second position.

In this aspect, the power can actuate any number of valves by any number of members. However, the at least two valves can be provided by a single motive member. The single motive member can provide a rotary valve. Alternatively, the motive member can include a piston member.

The timer can be provided as a mechanical or electromechanical timer. The timer can be provided by a microcircuit. In this regard, it is contemplated that at least a portion of the switch can also be provided by the microcircuit.

In still another aspect, the invention has a feeding and decompression device providing substantially constant aspiration during feeding yet does not require a solenoid valve and a timer. In this aspect, the invention incorporates a single aspirate reservoir and provides constant aspiration and feeding by a means other than switching between two or more such reservoirs. In this aspect, a feeding and decompression device includes at least one aspirate reservoir having an aspiration port and a feeding port. An aspiration channel is connected to the aspirate reservoir via the aspiration port. A feeding channel is connected to the aspirate reservoir via the feeding port. A vacuum source is connected to the aspiration channel for drawing aspirate toward the aspirate reservoir. The vacuum source in this aspect of the invention can be provided by an electric pump fluidly connected directly to the aspiration channel.

The invention includes a method of feeding and decompressing. In particular, the invention includes a method of feeding and decompressing in a gastro-intestinal tract. The method includes initial steps of placing a distal end of a feeding channel at a first position and a distal end of an aspiration channel at a second position that is spaced proximally relative to the first position. In accordance with the method, digestive juices and any nutrient or feeding material therein are continuously aspirated via the aspiration channel. In accordance with one aspect of the method, the step of continuously aspirating further comprises substantially collapsing a portion of the jejunum at the second position. The method further comprises continuously feeding via the feeding channel.

In one aspect of the method, the steps of continuously aspirating and continuously feeding further include aspirating into at least one of a plurality of aspirate reservoirs at a time through the aspiration channel. In accordance with the method, the aspiration channel can be common to all of the aspirate reservoirs.

In another aspect of the method, the step of continuously feeding includes feeding from one of the plurality of aspirate reservoirs into which nothing is being aspirated. That is, aspirate can be directed into other(s) of the plurality of aspirate reservoirs simultaneously with the step of feeding from the one aspirate reservoir into the feeding channel. The method further includes supplying the feeding channel with feeding material from an unused feeding material line and from at least one refeeding line connected to another of the aspirate reservoirs.

In still another aspect of the method, the step of continuously feeding further comprises returning at least a portion of digestive juices and feeding material to the first position that were previously aspirated at the second position. This return of digestive juices reduces the tendency of dehydration in a patient. The return of the feeding material reduces waste of the material. However, this refeeding and feeding must be accomplished in a way that avoids physiological harm and discomfort. Therefore, the method of feeding and decompressing further includes inhibiting distending of the gastro-intestinal tract. This is achieved by limiting an amount of aspirate that is fed and refed into the feeding channel during a certain period of time. As such, the method not only includes simultaneously impeding overfeeding, distending, and dehydration, but also facilitates obtaining direct feedback regarding absorption of a feeding material in the gastro-intestinal tract. This feedback can be in the form of observing a volume of aspirate that is greater than a predetermined amount. Thus, the method can also include adjusting the pressure or the flow resistance in the feeding channel so that a volume of aspirated fluid during a period of time is substantially equal to or less than the volume absorbed during the same period of time.

Other advantageous aspects of the method are improving an efficiency of digestion and absorption by removing gases from a gastro-intestinal tract and by stepping a feeding material forward in the gastro-intestinal tract to a location where greater peristaltic activity facilitates absorption. As can be appreciated, the efficiency can be improved to a case specific and time dependent maximum by the steps of observing and adjusting as set forth above. To this end, the volume of aspirate returned plus the unused feeding material to be fed can be made to be substantially equal to the volume absorbed. As long as the sum of the fluid to be fed is not greater than the fluid being absorbed, overfeeding will be avoided.

The combination feeding and decompression or aspiration tube can be formed as a feeding tube assembly that overcomes deficiencies of past devices and provides a readily assembleable unit that can be put together by a doctor or an assistant in a hospital. Thus, the expensive plural-lumen feeding and aspirating tubes of the past can be replaced by a simple combination of an inner and an outer tube assembled together to form the feeding tube of the present invention. In particular, this feeding tube can be a jejunal feeding and aspirating tube for the several reasons and specifics set forth herein.

In a simple form, the feeding and aspirating tube assembly includes a first outer aspirating tube and a second inner feeding tube. The second inner feeding tube is removably disposed inside the first outer aspirating tube. The outer tube has a branch portion having at least two branches. One of the branches can be selectively used to guide an inner tube through an external opening and into an interior of the outer tube. The other of the branches can be connected to a vacuum or pump source for aspirating therethrough from within the outer tube.

Many of the aspects of the present invention provide the advantage of enabling feeding of a fine feeding material and closely monitoring a patient and the amount of feeding material being absorbed in the early stages after an operation. Subsequent to this feeding and monitoring period, when a patient's gastro-intestinal tract is capable of consistently absorbing more feeding material, the fine feeding material can be replaced by a coarser feeding material and the combination feeding and aspirating tube can be replaced by a subset of the feeding and aspirating tube combination. That is, the feeding tube can be withdrawn from within the outer aspirating tube and the aspirating tube can be used for both feeding courser feeding material and for aspirating. Alternatively, a separate feeding tube can be used to feed the courser material.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

Figure 1:
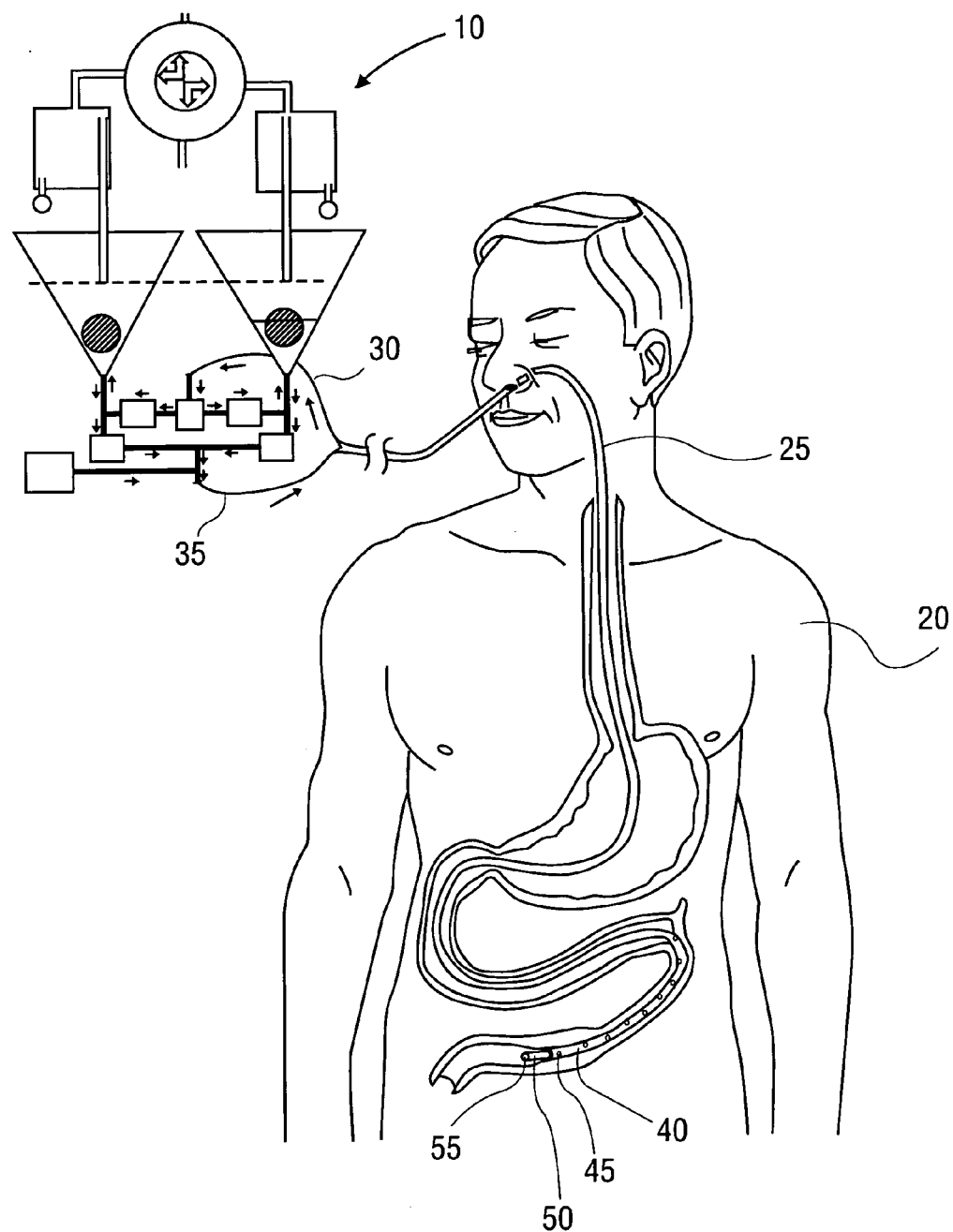
FIG. 1 is a diagrammatic view of a system including a device according to a first embodiment of the present invention, depicting a use for feeding and decompressing in a gastro-intestinal region of a patient.

As discussed above, embodiments of the present invention relate to devices and methods for feeding and decompressing in a gastro-intestinal tract. As shown in FIG. 1, an aspirate storing and refeeding device 10 is used to feed and decompress in a gastro-intestinal tract 15 of a patient 20. To this end, a combination feeding and aspirating tube 25 is inserted into the gastro-intestinal tract 15 through the nose and esophagus. Other ways of accessing the gastro-intestinal tract include inserting the tube through the abdominal wall directly into the jejunum, or directly into the stomach and intraluminally to the jejunum. As can be appreciated from FIG. 1, the combination feeding and aspirating tube 25 is a double lumen tube and comprises an aspiration channel 30 and a feeding channel 35 for handling flow in opposite respective directions. Combining these channels 30, 35 into a single composite tube 25 has the advantage of reducing bulk and complexity in the inserted portion of the channels 30, 35. The aspiration channel 30 has a distal end 40 including an opening 45 for aspirating fluids including digestive juices and feeding material. Additional openings located at spaced intervals proximally from the distal end 40 along the aspiration channel 30 may be provided. This has the effect of aspirating along a greater length of the gastrointestinal tract as indicated by the collapsed region shown in FIG. 1. The feeding channel 35 has a distal end 50 extending distally beyond the distal end 40 of the aspiration channel 30. The distal end of the feeding channel 35 has an opening 55 for delivering feeding material and other fluids as will be described below. Preferably, the distal end 50 and the opening 55 of the feeding channel 35 is spaced distally from the distal end 40 and opening 45 of the aspiration channel 30 by approximately ½ inch. Depending on the particulars of the cite at which the channels are placed, the separation of the most distal openings 45, 55 may be in the range from ¼ inch to 12 inches. In most cases, the separation of the distal openings 45, 55 of the aspirating and feeding channels 30, 35 will not exceed approximately 6 inches.

In one embodiment, the device 10 comprises a first aspirate reservoir 60 and a second aspirate reservoir 65. The reservoirs 60, 65 can be provided in the form of burettes having single lumen combination feeding and aspirating lines 70, 75 for handling both aspiration and refeeding of aspirate to and from the reservoirs 60, 65, respectively. The combination feeding and aspirating lines 70, 75 generally handle flow in only one direction at a time, either toward or away from the reservoirs 60, 65. However, flow in one of the combination feeding lines is generally in an opposite direction relative to flow in the other of the combination feeding and aspirating lines 70, 75. Thus, there is an alternating pattern of aspirating into the first reservoir 60 for a first half of a cycle and then aspirating into the second reservoir 65 for a second half of the cycle. Meanwhile, the second reservoir 65 refeeds aspirate for the first half of the cycle and the first reservoir 60 refeeds aspirate for the second half of the cycle. This alternating pattern can be repeated indefinitely during feeding. It is to be understood that refeeding need not be continuous during all of the half cycles. Likewise, aspiration flow may cease at any point during each of the half cycles. Additionally, the cycles need not be divided into halves. Rather any alternating pattern of time is considered to be within the scope of the invention.

Figure 2:
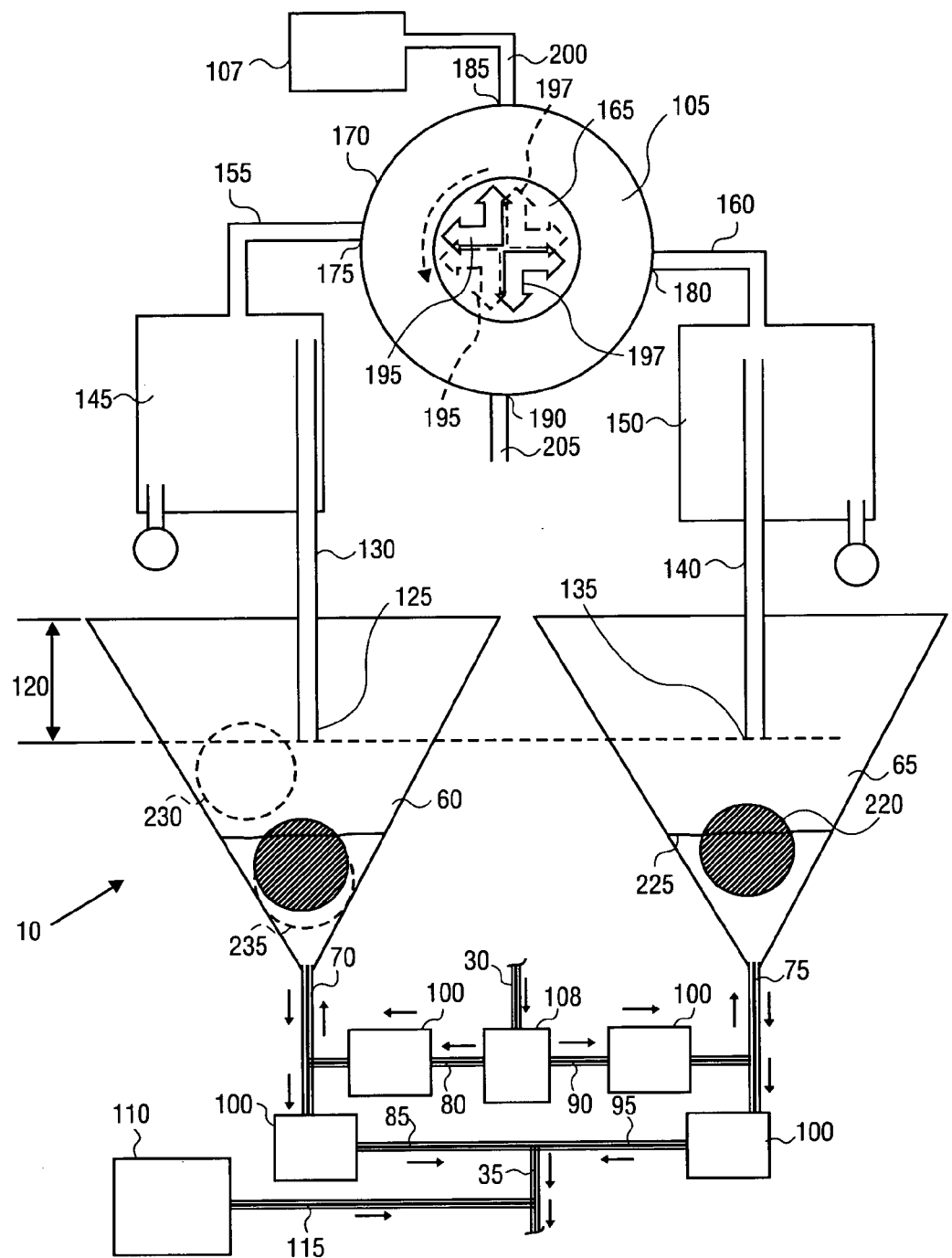
FIG. 2 is an enlarged diagrammatic view of the device of the embodiment shown in FIG. 1.

In order to effectuate the alternating pattern of aspirating and refeeding, the device includes a system of lines 80, 85, 90, 95, one-way valves 100, and a solenoid valve 105 for alternatingly connecting the reservoirs to a vacuum source 107. The one-way valves 100 permit flow in the lines 80, 85, 90, and 95 only in the directions indicated by the arrows in FIG. 2. Thus, when the solenoid valve 105 connects either of the reservoirs 60, 65 with the vacuum source 107, only flow through the aspirating lines 80 and 90 is induced, which in turn induces flow from the aspiration channel 30. When the vacuum source 107 is disconnected from one of the reservoirs 60, 65, the contents of that reservoir are permitted to flow out through one of the feeding lines 85, 95, preferably under the influence of gravity. Alternatively, a pump or vacuum source 107 could be connected to the feeding channel 35 to draw and refeed the aspirate into the feeding channel 35. A filter 108 can also be placed in the aspiration channel 30 or between the aspiration channel 30 and the aspirating lines 80, 90 as shown in FIG. 2.

As shown, the device 10 is in addition to the feeding system that is typically used in hospitals. As such, a feeding material is provided in a feeding bag 110. The feeding bag is connected to the feeding channel by an unused feeding material line 115. The flow of the feeding material into the feeding channel 35 is affected by the capacity of the feeding channel 35, the pressure at which the feeding material is fed from the feeding bag 110, (such as by a pump), and the flow rate of the aspirate that is being refed into the feeding channel 35. These and other factors can be adjusted to adjust the flow of feeding material into the feeding channel. Preferably, the flow from the feeding bag 110 can be reduced in proportion to a flow of aspirate that is refed. Thus, waste of unused feeding material is avoided. Furthermore, nutrients and digestive juices that typically have been discarded in the past can be reintroduced and absorbed with little or no loss of fluids and nutrients.

The device 10 also enables the aspiration to be applied continuously. That is, vacuum from the vacuum source can be applied substantially constantly. Flow of the aspirate may not be constant or continuous due to a presence or a lack of presence of fluids in the portion of the gastrointestinal tract being aspirated. However, continuous and/or constant aspiration has the advantage of continuously removing gases from the gastrointestinal tract as there is no interval without suction during which gas may be propelled by peristalsis distal to the most distal aspiration orifice. Removing these gases has the advantages set forth above. Furthermore, removing the gases continuously or constantly has the advantage of preventing distending of the intestines due to build up of these gases.

Ideally, when the length of the half cycles are set properly, both refeeding flow and aspiration flow can be continuous, if not constant. With more constant and/or continuous flow in the feeding channel, the fluctuation of flow into the gastrointestinal tract is reduced. By providing less fluctuation in the flow into the intestines, distending can further be prevented. Furthermore, nutrients and fluids will be more constantly available for absorption by the intestines.

A predetermined volume of aspirate to be retained in the reservoirs 60, 65 can be selected and set. This volume also affects the "head" or pressure due to gravitational forces that causes the flow of aspirate out of the reservoirs 60, 65. Preferably, a maximum predetermined volume to be retained in each reservoir 60, 65 during each half cycle is in the range from 10 to 15 cc. This reduces the chance for overfeeding, for example when the half cycle is kept to approximately ½ minute. Perhaps a maximum adjustable volume could be as much as 35 cc. Adjustment of the predetermined volume is achieved by adjusting the depth 120 of a lower end 125 of a first draw tube 130 in the first aspirate reservoir 60. Similarly, the maximum volume of aspirate to be retained in the second aspirate reservoir 65 can be adjusted by adjusting a depth 120 of a lower end 135 of a similar second draw tube 140.

The draw tubes 130, 140 connect the aspirate reservoirs 60, 65 to first and second overflow chambers 145, 150. These tubes also provide fluid communication between an interior of each of the reservoirs 60, 65 and the solenoid valve 105. Thus, draw tubes 130, 140 connect the aspirate reservoirs to the vacuum source 107 in an alternating pattern as will be described in further detail below. The draw tubes 130, 140 act to remove aspirate in excess of the predetermined maximum volume and draw the excess aspirate into respective overflow chambers 145, 150. The overflow chambers 145, 150 may have any reasonable volume. Preferably, the volume of each overflow chamber is in the range from 200–4000 cc, with 1000 cc being a fairly standard capacity. Once removed, the excess aspirate can be discarded or refed later when the flow of aspirate from the aspiration channel 30 has decreased.

The first and second overflow chambers 145, 150 are connected to the solenoid valve by first and second valve connection lines 155, 160. Thus, the overflow chambers 145, 150 are fluidly connected to the solenoid valve 105 and to the reservoirs 60, 65 via the draw tubes 130, 140. The solenoid valve preferably comprises a single motive member 165 contained within a solenoid housing 170. The motive member 165 provides at least two (2), two-way valves for connection between at least four ports 175, 180, 185, and 190. Preferably, the motive member has first and second channels 195 and 197. The first channel 195 connects the first valve connection line 155 from the first aspirate reservoir 60 to the vacuum source 107 through a vacuum line 200 or to an ambient pressure volume through a vent hose 205. The second channel of the motive member 165 connects the second valve connection line 160 to the ambient pressure volume through the vent line 205 or to the vacuum source 107 through the vacuum line 200. In one configuration of the solenoid valve, the motive member 165 is a rotary member that rotates under the influence of a solenoid through a range of approximately ninety degrees to exclusively connect either the first aspirate reservoir 60 or the second aspirate reservoir 65 to the vacuum source 107 as shown in FIG. 2. Alternatively stated, the first channel either connects the first reservoir 60 to the vacuum line 200 or to the vent line 205. Likewise, the second channel 197 of the motive member 165 either connects the second aspirate reservoir 65 to the vent line 205 or to the vacuum line. Only one of the reservoirs 60, 65 is connected to the vacuum source 107 at a time. The other reservoir is connected to ambient air through the vent line 205. By way of example and not by way of limitation, this is efficiently achieved by a single motive member that rotates or moves linearly between only two operating positions.

Figure 3:
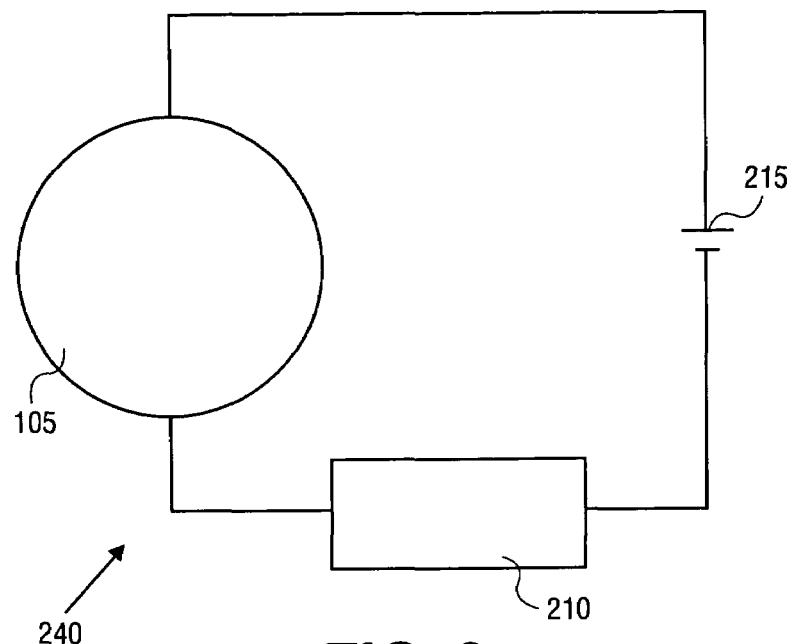
FIG. 3 is a schematic representation of the solenoid valve and switch device that is included in the device of FIGS. 1 and 2.

The connections to the vacuum source 107 and vent 205 are alternated back and forth so that one of the aspirate reservoirs 60, 65 is connected to the vacuum source 107 and the other is connected to the vent at all times. Preferably, this is achieved by a switch connected to the solenoid valve 105, and wherein the solenoid valve is in a first position when the switch is closed and in a second position when the switch is opened. That is, applying power to the solenoid valve places it in a first position and removing power from the solenoid valve places it in a second position indicated by the dashed arrows in FIG. 2. Preferably, the switch is provided by a timer switch 210 in a circuit connected to a power source 215 as shown in FIG. 3. The timer switch 210 can be adjusted to actuate its switch at a predetermined interval corresponding to a half cycle. Thus, the switch 210 will be turned on or off after each half cycle and the motive member 165 will be moved to its first or second position.

The solenoid could be replaced by a different solenoid valve. For example, the solenoid valve may comprise a piston member and more than four ports. The solenoid valve can connect the aspirate reservoirs to respective sources of vacuum and/or to respective vent lines. Further alternatively, the device could be manually operated. That is, instead of employing a timer switch, a switch could be operated by hand. Further alternatively, manually operated valves could be provided so that a person would be required to switch the connections to the reservoirs back and forth between vacuum and vent.

As indicated above, the amount of aspirate received into the reservoirs 60, 65 optimally is equal to or slightly less than the amount refed during a half cycle of the device. However, the amount refed varies during feeding and over the course of recuperation. Therefore, there will be periods of time during some half cycles when the aspiration is being applied, but little or no aspirate is flowing. Likewise there will be periods when the aspirate being refed is completely withdrawn from a reservoir before a current half cycle has ended. Since a reservoir is connected to ambient during feeding from that reservoir, there is a potential for drawing air from the ambient into the feeding channel and eventually into the gastrointestinal tract. To prevent this from happening, a check valve is provided in each reservoir 60, 65 by a ball 220. As shown, the ball 220 is buoyant and is thus positioned by the aspirate at a first level 225. When the aspirate reaches a maximum level, the ball floats at the maximum aspirate level as indicated at 230. However, when the aspirate completely leaves the reservoirs 60, 65, the ball 220 seats in a sealed position as shown at 235. With aspirate refeed being induced by gravity, this type of check valve will normally be sufficient to prevent air from being drawn into the feeding channel 35. On the other hand, if a positive pressure pump is employed to draw and refeed the aspirate, a more positive shutoff valve may be necessary.

As can be appreciated, the device 10 includes solenoid valve and timer device 240 as shown in FIG. 3. Furthermore, the solenoid valve and timer device 240 has special characteristics that are particularly beneficial when used with the overall device 10 described above. Specifically, the solenoid valve 105 could be made automatic by an electrical circuit including a timer switch 210. The timer switch can comprise microcircuitry that includes a timer. The timer switch 210 can further include low voltage switch actuation that opens and closes the circuit connected to the power source 215. Alternatively, the timer switch can be made up of discrete electrical components that accomplish the same alternating timing function. Further alternatively, the timer switch can include a combination of electrical and mechanical elements that achieve the same alternating timing function.

Figure 4:
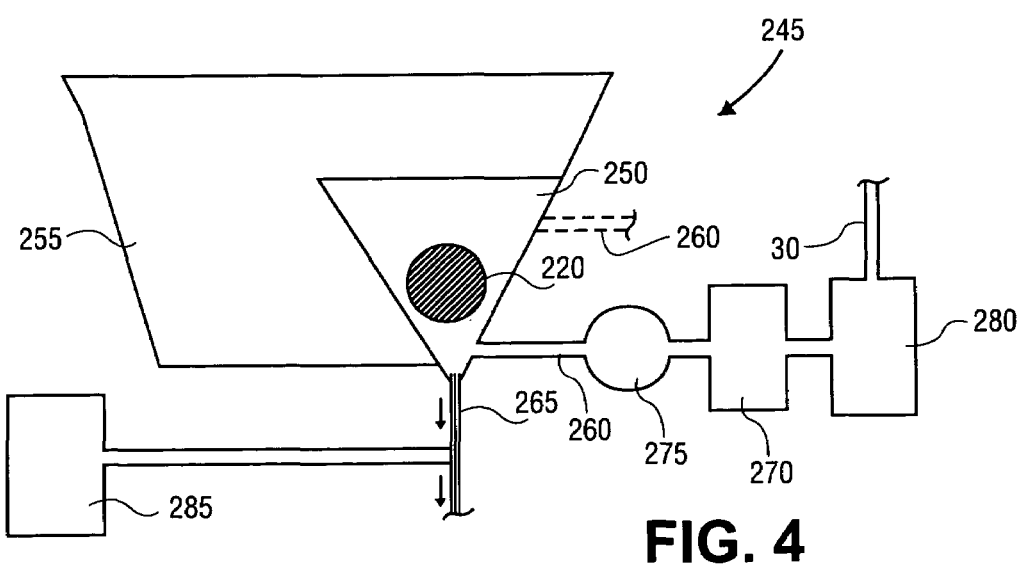
FIG. 4 is a diagrammatic view of a device according to a second embodiment of the invention.

FIG. 4 is a diagrammatic view of a device 245 according to a second embodiment of the invention. This device 245 differs from the device 10 described above in that the previously described device had two aspirate reservoirs whereas the device 245 has only one aspirate reservoir 250. The aspirate reservoir 250 in this case has a capacity equal to a maximum volume of aspirate to be retained in the reservoir. Any excess aspirate will spill into an overflow chamber 255. A further difference is that the line connected to the reservoir 250 for refeeding aspirate does not also function to conduct aspirate to the reservoir 250. That is, the aspirate channel 30 is connected to the reservoir by an aspirating line 260 and the feeding channel 35 is connected to the reservoir 250 by an aspirate refeeding line 265. As such, aspiration and refeeding can occur simultaneously from the same reservoir 245. However, aspiration cannot be effectuated by a vacuum source in fluid communication with the aspiration channel via the reservoir 245. If so, refeeding in the refeeding line 265 would be impeded. Therefore, a positive pressure pump 270 is provided in the aspirating line to draw aspirate toward the reservoir 245. Aspirate can be refed by a gravitational force. However, a pressure source such as a pump could be substituted. To assure flow in the right direction, a one way valve 275 is also placed in the aspirating line 260. As in the previous embodiment a filter 280 is also preferably placed in the aspirating line 260, or between the aspirating line 260 and the aspiration channel 30. A check valve including a ball 220 like that described in the embodiment above is provided in the reservoir 250 of the device 245. This check valve functions substantially the same as that described above. Typically, the reservoir is open to the ambient air so that aspirate can be refed by gravity. Like the previous embodiment, the device is intended to be used in addition to a supply of an unused feeding material that can be fed from a feeding bag 285 by a pump or gravity.

The device 245 of FIG. 4 is similar to the previously described embodiment in that it advantageously provides for continuous or constant aspiration and refeeding of aspirate. While the device 245 requires a positive pressure source 270, device 245 does not require the solenoid and timer device 240 of the previously described embodiment of FIGS. 1–3.

Figure 5:
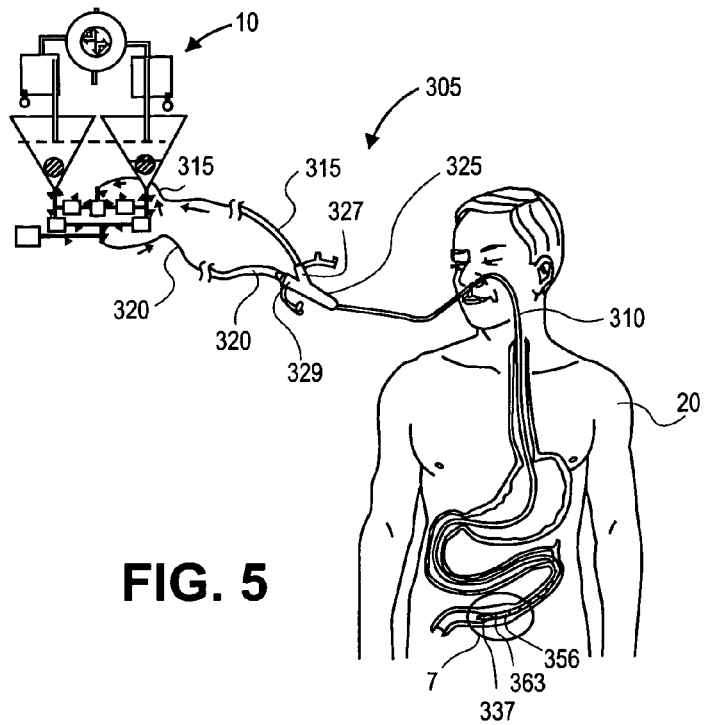
FIG. 5 is a diagrammatic view of the system of FIGS. 1–2 and incorporating a particular feeding tube assembly in accordance with one aspect of the invention.

FIG. 5 shows a particular feeding tube assembly 305 that can be used with the device 10 of FIGS. 1 and 2 or with the device 245 of FIG. 4. The feeding tube assembly 305 can also be used with other feeding and aspirating devices. For example, the feeding tube assembly 305 can be used together with the single burette system of my U.S. Pat. No. 6,447,472 issued Sep. 10, 2002, which is incorporated herein by reference. The feeding tube assembly 305 has a combination feeding and aspirating tube 310 that is connected to the feeding and aspirating device 10 by a separate aspirating line 315 and a separate feeding line 320. The feeding tube assembly 310 includes a branched section 325 that includes at least a first branch 327 and a second branch 329. As shown in FIG. 5, the first branch 327 can be selected for connection with the separate aspirating line 315, and the second branch 329 can be selected for connection with the separate feeding line 320.

Figure 6:
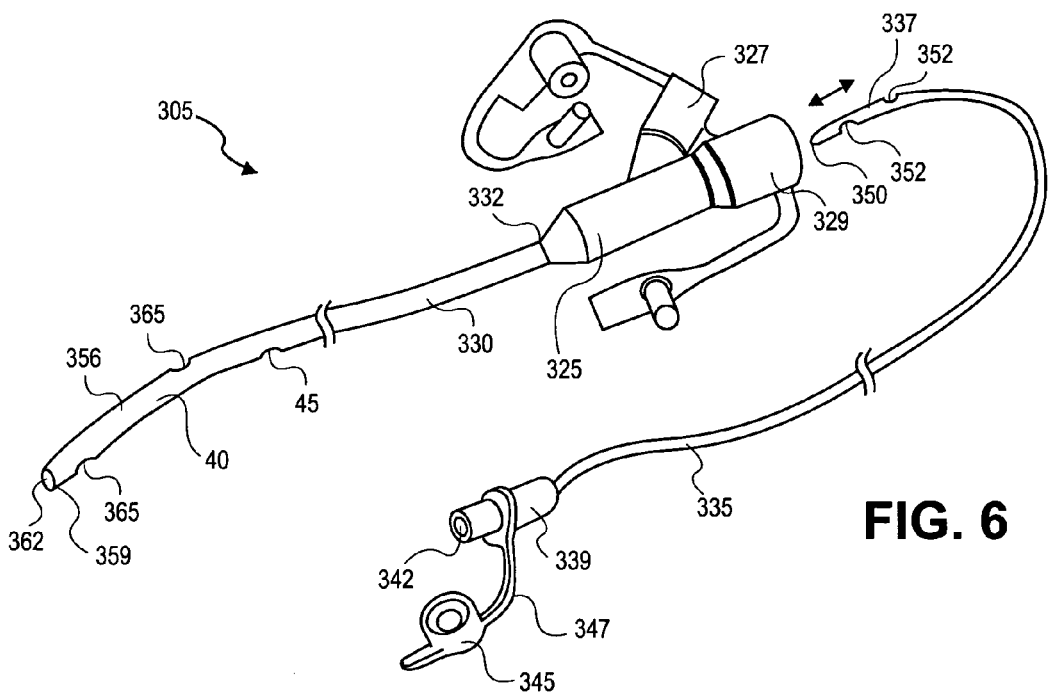
FIG. 6 is an exploded perspective view of the feeding tube assembly of FIG. 5.

FIG. 6 shows the feeding tube assembly 305 in greater detail. A first outer tube 330 is connected to the branched section 325, which in this case is in the form of a "Y". The first outer tube 330 is connected to the branched section by a sealed joint 332. A second inner tube 335 is selectively inserted into the outer tube 330 via the branched section 325. Respective lengths of the inner tube 335 and the outer tube 330 are selected to provide a distally protruding portion 337 of the inner tube 335 when the inner tube is inserted completely through the outer tube 330 as shown in FIG. 5. This relationship provides for a distally located position of the feeding portion of the feeding and aspirating tube 310 relative to the aspirating portion as will be described in greater detail below.

It is to be understood that when the inner tube 335 is inserted to its assembled state within the outer tube 330, an adapter 339 on the inner tube 335 is received in the second branch 329 in a hermitically sealed relation. Thus, no aspirate or feeding material can move in or out of the second branch 329 except through the inner tube 335. For this purpose, the adapter 339 has an input opening 342 on a proximal end thereof for receiving and passing a feeding material into the inner tube 335. A cap 345 connected to the adapter 339 by a flexible connector 347 can be used to close the input opening 342 when the inner feeding tube 335 is not in use. The inner tube 335 has a rounded distal end 350 to aid in passing the inner tube 335 through the outer tube 330 and to reduce the chance of injury to an intestinal tract of a patient. The inner tube 335 has feeding openings 352 slightly proximately located relative to the rounded distal end 350 and spaced along the inner tube 335 in an alternating pattern as shown in FIG. 6.

Figure 7:
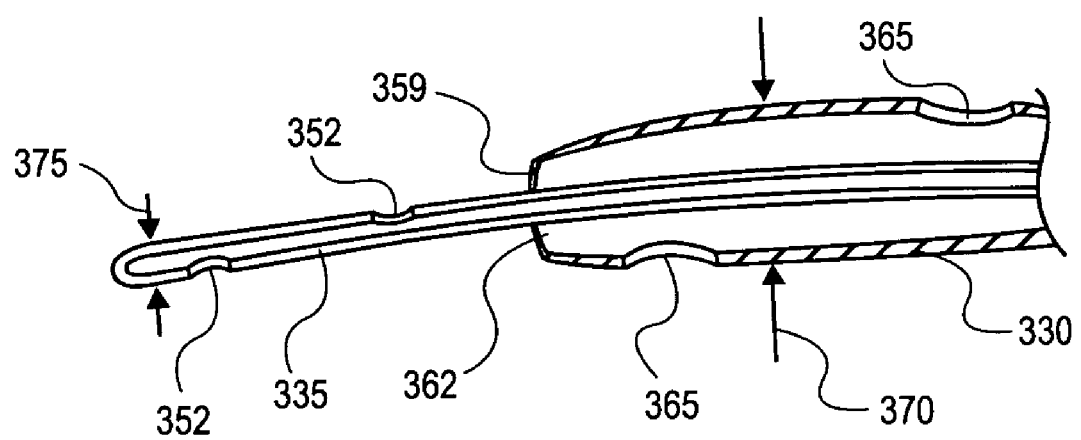
FIG. 7 is sectional view of an encircled portion indicated at 7 in FIG. 5.

The outer tube 330 has a distal portion 356 including a distal tip 359 that has an aspirating opening 362 therethrough. Additional aspirating openings 365 are spaced along the outer tube 330 in an alternating relation as shown in FIG. 6. FIG. 7 is a sectional view of a portion of the feeding tube 310 shown as in an encircled region shown at 7 in FIG. 5. This figure shows how the feeding openings 352 can be spaced along the inner tube 335. Likewise, the aspirating openings 365 can be spaced along the outer tube 330. As described with regard to the embodiments above the feeding openings need to be located distally relative to the aspirating openings 365. This provides the advantage of feeding at a location downstream in the gastrointestinal tract from a location at which excess gastrointestinal fluids and feeding material are aspirated. Thus, the feeding material and any medication in the inner tube 335 is less likely to be withdrawn during aspiration. This is especially so when the feeding tube is placed in the jejunum as described above.

In this particular embodiment of the feeding and aspirating tube combination 310, the feeding openings 352 are located at distal positions within a particular range of distances from the most distal aspirating opening 362 of the aspirating outer tube 330. As shown in FIG. 7, a distal most feeding opening 352 is located in a range from approximately 2 cm to approximately 3 cm from the distal opening 362 of the outer aspiration tube 330. The feeding opening 352 that is most proximal is located in a range from approximately ½ cm to approximately 2 cm from the distal opening 362 of the outer tube 330.

The relative sizes of the inner tube 335 and the outer tube 330 are important in determining the resistance to flow between the inner tube 335 and the outer tube 330. For example, if the inner tube 335 is too large, then the flow of aspirate between the inner tube 335 and the outer tube 330 will be adversely restricted. Thus an outer diameter 370 of the outer aspirating tube 330 should have a dimension in a range from approximately 10 French–18 French. In more common units, the outside diameter 370 of the outer aspirating tube 330 can be in a range from approximately 3 mm to approximately 6 mm. The outer diameter 375 of the inner tube 335 can be in a range from approximately 4 French to approximately 8 French. Likewise, in more common units the outer diameter 375 of the inner tube 335 can be in a range from approximately 1 mm to approximately 3 mm. In one particular configuration, the outer diameter 375 of the inner tube 335 is approximately 6.5 French and the outer diameter 370 of the outer tube 330 is approximately 14 French.

While the inner tube 335 and the outer tube 330 are in their assembled state the relationship between the inner tube 335 and the outer tube 330 can be considered generally coaxial. This is the case even when the outer tube 330 fits loosely around the inner tube 335 to permit aspiration through the outer tube 330 while the inner tube 335 is disposed inside the outer tube 330. Advantageously, the inner tube is removable from the outer tube. Thus, the inner tube 335 and the outer tube 330 form the assembly 305 that can be joined together as a combination feeding and aspirating tube 310 by an end user such as a surgeon or an assistant in a hospital or other facility. As such, a method of feeding and aspirating with a feeding tube of the present invention includes the step of inserting an inner tube 335 through an outer tube 330. The method further includes sealing an external end of the inner tube relative to an external end of the outer tube. The method also includes placing the combination inner and outer tubes in the jejunum of the patient. This placement of the combination feeding and aspirating tube can be performed in any of the various manners set forth above. However, it is to be understood that a small amount of feeding material can be fed during insertion in order to prevent clogging of the inner tube by clotted blood or large particles from the gastro intestinal tract. The method can also include aspirating through the outer tube.

In another aspect of the invention, the method includes feeding for a first predetermined period of time after an operation. After the first predetermined period of time has lapsed, the inner tube is removed. Feeding can subsequently be provided through the outer tube or through another separate feeding tube that is larger than the inner tube. The first predetermined period of time can correspond to a period of time in which the patient recovers sufficiently for the gastrointestinal tract to be capable of accepting larger quantities of feeding material, and perhaps a courser feeding material. After the operation and before the first predetermined period of time has lapsed, feeding must be monitored closely in order to avoid overfeeding. Once the gastrointestinal tract function is capable of consistently absorbing the feedings, then the monitoring can be lessened or stopped. Once the feedings are being readily absorbed and monitoring has been stopped, the more costly two-reservoir system is no longer needed. Also, as the gastrointestinal tract becomes more capable of handling courser feedings, the expensive predigested feedings are no longer required. Therefore, less expensive feeding material can be fed and constant monitoring is no longer required.

It is to be understood that the term "positive pressure source" generally refers to a pump or an equivalent, such as a syringe or pressurized receptacle. The term "positive" refers to an "active" as opposed to a passive pressure means, such as a gravitational pressure means. It is also to be understood that vacuum source refers to any number of equivalents such as a pump, an aspirating syringe, or a negative pressure receptacle. One common vacuum source is that typically provided by a hospital or other facility and piped throughout the facility to the various stations including patients' rooms.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

What is claimed is:

1. A method of feeding and aspirating comprising:
   inserting an inner tube through an outer tube;
   sealing an external end of the inner tube relative an external end of the outer tube;
   placing the combination inner tube and outer tube in the jejunum of a patient so that each of an internal end of the inner tube and an internal end of the outer tube are positioned in the jejunum;
   feeding from externally of the patient through the inner tube to the jejunum of the patient; and
   aspirating from the jejunum through the outer tube.

2. The method of feeding and aspirating of claim 1, wherein:
   the step of feeding comprises feeding for a first predetermined period of time after an operation;
   the method of feeding and aspirating further comprises:
      removing the inner tube from the outer tube after the first predetermined period of time; and
      feeding through one of the outer tube and another separate feeding tube.

3. The method of feeding and aspirating of claim 1 wherein:
   the step of feeding further comprises feeding for a first predetermined period of time after an operation;
   the method of feeding and aspirating further comprises:
      removing the inner tube from the outer tube after the first predetermined period of time; and
      at least one of feeding and aspirating through the outer tube after the first predetermined period of time.

* * * * *